(12) United States Patent
Wu et al.

(10) Patent No.: US 7,214,825 B2
(45) Date of Patent: May 8, 2007

(54) O-(3-CHLOROPROPENYL) HYDROXYLAMINE FREE BASE

(75) Inventors: Baihua Wu, Newark, DE (US); Kevin P Keller, West Chester, PA (US); Steven C Barr, West Chester, PA (US); Daniel F Smith, Glen Mills, PA (US)

(73) Assignee: Honeywell International Inc., Morristown, NJ (US)

(*) Notice: Subject to any disclaimer, the term of this patent is extended or adjusted under 35 U.S.C. 154(b) by 65 days.

(21) Appl. No.: 10/688,279

(22) Filed: Oct. 17, 2003

(65) Prior Publication Data

US 2005/0085645 A1   Apr. 21, 2005

(51) Int. Cl.
C07C 239/20 (2006.01)

(52) U.S. Cl. .................................. 564/300; 564/301

(58) Field of Classification Search ............... None
See application file for complete search history.

(56) References Cited

U.S. PATENT DOCUMENTS

| | | |
|---|---|---|
| 3,941,741 A | 3/1976 | De Zuba et al. |
| 3,950,426 A | 4/1976 | Culbertson |
| 3,957,756 A | 5/1976 | Ribka et al. |
| 3,960,865 A | 6/1976 | Culbertson |
| 3,962,201 A | 6/1976 | Dulog et al. |
| 3,984,438 A | 10/1976 | Greenbaum et al. |
| 3,996,285 A | 12/1976 | Culbertson |
| 4,001,318 A | 1/1977 | Botta |
| 4,006,155 A | 2/1977 | Sullivan |
| 4,010,209 A | 3/1977 | Smith et al. |
| RE29,195 E | 4/1977 | Brady |
| RE29,196 E | 4/1977 | Winn |
| 4,025,349 A | 5/1977 | Mee |
| 4,026,884 A | 5/1977 | Mee |
| 4,059,432 A | 11/1977 | Takematsu et al. |
| 4,064,185 A | 12/1977 | Johnson et al. |
| 4,080,496 A | 3/1978 | Mee |
| 4,092,347 A | 5/1978 | Schenk et al. |
| 4,101,557 A | 7/1978 | Mueller et al. |
| 4,119,780 A | 10/1978 | Sullivan |
| 4,129,599 A | 12/1978 | Escher et al. |
| 4,156,065 A | 5/1979 | Onder et al. |
| 4,180,505 A | 12/1979 | Toldy et al. |
| 4,185,115 A | 1/1980 | Albright et al. |
| 4,219,489 A | 8/1980 | Johnson et al. |
| 4,244,955 A | 1/1981 | Farr et al. |
| 4,287,348 A | 9/1981 | Kitzing et al. |
| 4,315,071 A | 2/1982 | Fitzgerald |
| 4,350,822 A | 9/1982 | Albright et al. |
| 4,440,566 A | 4/1984 | Luo |
| 4,482,740 A | 11/1984 | Iwataki et al. |
| 4,486,586 A | 12/1984 | Narita et al. |
| 4,524,128 A | 6/1985 | Edwards et al. |
| 4,526,608 A | 7/1985 | Lee |
| 4,596,877 A | 6/1986 | Becker et al. |
| 4,602,935 A | 7/1986 | Becker et al. |
| 4,604,210 A | 8/1986 | Lin |
| 4,617,050 A | 10/1986 | Jahn et al. |
| 4,623,381 A | 11/1986 | Jahn et al. |
| 4,626,276 A | 12/1986 | Luo |
| 4,631,081 A | 12/1986 | Watson et al. |
| 4,636,245 A | 1/1987 | Wroblowsky et al. |
| 4,654,073 A | 3/1987 | Jahn et al. |
| 4,659,362 A | 4/1987 | Watson et al. |
| 4,659,814 A | 4/1987 | Palomo-Coll et al. |
| 4,668,275 A | 5/1987 | Keil et al. |
| 4,678,504 A | 7/1987 | Schulz et al. |

(Continued)

FOREIGN PATENT DOCUMENTS

DE    32 18 315    12/1982

(Continued)

OTHER PUBLICATIONS

McGraw-Hill Dictionary of Chemical Terms, Sybil P. Parker ed., 1985, McGraw-Hill Book Company, NY, p. 99.*

(Continued)

Primary Examiner—Brian Davis

(57) ABSTRACT

An O-substituted hydroxylamine having the following general formula:

$$R^1—CHX—O—NH_2$$

wherein X is hydrogen or an alkyl; and $R^1$ is an unsubstituted or substituted phenyl, thienyl, furanyl, pyrrolyl or $—CR^2=CR^3R^4$; wherein $R^2$, $R^3$ and $R^4$ are hydrogen, halogen or alkyl. The O-substituted hydroxylamine exhibits at least one property selected from the group consisting of: essentially free of hydroxylamine; essentially free of any solvent; a water content of between about 0% to 90% by weight; and a high strength (as measured by mole of the O-substituted hydroxylamine per gram of sample) of between about 0.5 to 3.3-fold as much as a 40% O-substituted hydroxylamine salt solution, by weight. The O-substituted hydroxylamine further comprising at least one additional property selected from the group consisting of: a purity of between about 98% to 100%, based on gas chromatographic area; and a purity drop of less than about 1.2% after 78 days at 40° C. when the O-substituted hydroxylamine has a concentration of about 85% in water, based on gas chromatographic area. The O-substituted hydroxylamine is at least one isomer selected from the group consisting of cis, trans and a mixture thereof. The O-substituted hydroxylamine may also be reacidified to an O-substituted hydroxylamine salt free of hydroxylamine.

43 Claims, 1 Drawing Sheet

U.S. PATENT DOCUMENTS

| | | |
|---|---|---|
| 4,683,303 A | 7/1987 | Pfaendler |
| 4,701,205 A | 10/1987 | Omid et al. |
| 4,732,894 A | 3/1988 | King |
| 4,734,124 A | 3/1988 | Chang et al. |
| 4,740,237 A | 4/1988 | Jahn et al. |
| 4,741,768 A | 5/1988 | Frazier et al. |
| 4,751,295 A | 6/1988 | Oka et al. |
| 4,755,217 A | 7/1988 | Chang et al. |
| 4,761,172 A | 8/1988 | Jahn et al. |
| 4,761,174 A | 8/1988 | Chang et al. |
| 4,801,717 A | 1/1989 | Tessier et al. |
| 4,803,215 A | 2/1989 | Jensen-Korte et al. |
| 4,806,146 A | 2/1989 | Carter |
| 4,812,160 A | 3/1989 | Jahn et al. |
| 4,816,066 A | 3/1989 | Michaely et al. |
| 4,820,823 A | 4/1989 | Tanaka et al. |
| 4,835,312 A | 5/1989 | Itoh et al. |
| 4,863,504 A | 9/1989 | Hamaguchi et al. |
| 4,888,042 A | 12/1989 | Arai et al. |
| 4,892,855 A | 1/1990 | Mizuno et al. |
| 4,902,337 A | 2/1990 | Hirai et al. |
| 4,906,289 A | 3/1990 | Yoshida et al. |
| 4,909,835 A | 3/1990 | Tobler |
| 4,914,124 A | 4/1990 | Muller et al. |
| 4,923,989 A | 5/1990 | Watson et al. |
| 4,939,278 A | 7/1990 | Anderson-McKay et al. |
| 4,954,160 A | 9/1990 | Gilkerson et al. |
| 4,965,390 A | 10/1990 | Schneider |
| 4,971,989 A | 11/1990 | Jensen-Korte et al. |
| 4,983,210 A | 1/1991 | Rheinheimer et al. |
| 4,987,996 A | 1/1991 | Wyss et al. |
| 4,994,106 A | 2/1991 | Kolassa et al. |
| 5,006,158 A | 4/1991 | Carter et al. |
| 5,006,159 A | 4/1991 | Markley et al. |
| 5,039,770 A | 8/1991 | Lindert et al. |
| 5,041,613 A | 8/1991 | McCombs |
| 5,074,903 A | 12/1991 | Jahn et al. |
| 5,075,504 A | 12/1991 | Schneider |
| 5,085,688 A | 2/1992 | Michaely et al. |
| 5,086,187 A | 2/1992 | Anderson-McKay et al. |
| 5,108,488 A | 4/1992 | Etheridge |
| 5,116,912 A | 5/1992 | Lindert et al. |
| 5,120,849 A | 6/1992 | Wild et al. |
| 5,128,465 A | 7/1992 | Kamiya et al. |
| 5,200,292 A | 4/1993 | Shinozaki et al. |
| 5,201,935 A | 4/1993 | Kolassa et al. |
| 5,225,589 A | 7/1993 | McCombs |
| 5,266,410 A | 11/1993 | Lindert et al. |
| 5,278,182 A | 1/1994 | Fujishima |
| 5,298,289 A | 3/1994 | Lindert et al. |
| 5,334,576 A | 8/1994 | Doehner, Jr. et al. |
| 5,359,126 A | 10/1994 | McCombs |
| 5,373,001 A | 12/1994 | Aszodi et al. |
| 5,395,845 A | 3/1995 | Benoit et al. |
| 5,397,779 A | 3/1995 | Aszodi et al. |
| 5,401,337 A | 3/1995 | Carlson et al. |
| 5,403,812 A | 4/1995 | Kast et al. |
| 5,405,865 A | 4/1995 | Benoit et al. |
| 5,407,896 A | 4/1995 | Kast et al. |
| 5,416,080 A | 5/1995 | Aszodi et al. |
| 5,434,175 A | 7/1995 | Babin et al. |
| 5,462,961 A | 10/1995 | Meki et al. |
| 5,484,934 A | 1/1996 | Ikeda et al. |
| 5,488,162 A | 1/1996 | Buckland |
| 5,514,642 A | 5/1996 | Misslitz et al. |
| 5,541,318 A | 7/1996 | Aszodi et al. |
| 5,557,013 A | 9/1996 | Keil et al. |
| 5,563,174 A | 10/1996 | Tomioka et al. |
| 5,576,054 A | 11/1996 | Brown |
| 5,578,622 A | 11/1996 | Ikeda et al. |
| 5,585,520 A | 12/1996 | Klein et al. |
| 5,599,771 A | 2/1997 | Wenger |
| 5,629,262 A | 5/1997 | Auxier et al. |
| 5,641,882 A | 6/1997 | Chemla |
| 5,674,810 A | 10/1997 | Theodoridis |
| 5,681,792 A | 10/1997 | Caulder et al. |
| 5,695,773 A | 12/1997 | Schapira et al. |
| 5,714,599 A | 2/1998 | Chemla |
| 5,723,665 A | 3/1998 | Kato et al. |
| 5,726,126 A | 3/1998 | Crews, Jr. et al. |
| 5,730,996 A | 3/1998 | Beall |
| 5,777,164 A | 7/1998 | Boaz |
| H1785 H | 2/1999 | Theodoridis |
| 5,877,186 A | 3/1999 | Leef et al. |
| 5,888,932 A | 3/1999 | Anderson et al. |
| 5,892,048 A | 4/1999 | Kishimoto et al. |
| 5,900,388 A | 5/1999 | Fenderson et al. |
| 5,936,083 A | 8/1999 | Aszodi et al. |
| 5,981,440 A | 11/1999 | Bratz et al. |
| 5,985,793 A | 11/1999 | Sandbrink et al. |
| 5,998,331 A | 12/1999 | Policello |
| 6,017,850 A | 1/2000 | Johnson et al. |
| 6,060,432 A | 5/2000 | Adams et al. |
| 6,083,873 A | 7/2000 | Fukada et al. |
| 6,083,881 A | 7/2000 | Nebel et al. |
| 6,093,680 A | 7/2000 | Gillespie et al. |
| 6,093,681 A | 7/2000 | Ward et al. |
| 6,103,667 A | 8/2000 | Brunner et al. |
| 6,107,254 A | 8/2000 | Rheinheimer et al. |
| 6,130,186 A | 10/2000 | Ward et al. |
| 6,133,202 A | 10/2000 | Bratz et al. |
| 6,147,030 A | 11/2000 | Mito |
| 6,177,138 B1 | 1/2001 | Sawaragi et al. |
| 6,184,182 B1 | 2/2001 | Gillespie et al. |
| 6,204,221 B1 | 3/2001 | Nebel et al. |
| 6,221,811 B1 | 4/2001 | Policello et al. |
| 6,239,072 B1 | 5/2001 | Flint et al. |
| 6,268,363 B1 | 7/2001 | Lee et al. |
| 6,274,536 B1 | 8/2001 | Nebel et al. |
| 6,291,399 B1 | 9/2001 | Henmi et al. |
| 6,300,281 B1 | 10/2001 | Whittington et al. |
| 6,313,139 B1 | 11/2001 | Dijcks et al. |
| 6,339,046 B1 | 1/2002 | Nebel et al. |
| 6,363,134 B1 | 3/2002 | Zondler et al. |
| 6,369,001 B1 | 4/2002 | Jimoh |
| 6,369,002 B1 | 4/2002 | Kunz et al. |
| 6,380,134 B1 | 4/2002 | Kunz et al. |
| 6,383,500 B1 | 5/2002 | Wooley et al. |
| 6,383,987 B1 | 5/2002 | Von der Heyde et al. |
| 6,399,542 B1 | 6/2002 | Henmi et al. |
| 6,410,480 B1 | 6/2002 | Muhlebach et al. |
| 6,417,357 B1 | 7/2002 | Tinkl et al. |
| 6,448,295 B1 | 9/2002 | Sikorski et al. |
| 6,451,823 B1 | 9/2002 | Sikorski et al. |
| 6,451,830 B1 | 9/2002 | Sikorski et al. |
| 6,455,519 B1 | 9/2002 | Sikorski et al. |
| 6,458,849 B1 | 10/2002 | Sikorski et al. |
| 6,458,852 B1 | 10/2002 | Sikorski et al. |
| 6,458,952 B1 | 10/2002 | South et al. |
| 6,462,092 B1 | 10/2002 | Sikorski et al. |
| 6,469,198 B2 | 10/2002 | Suzukamo et al. |
| 6,472,526 B1 | 10/2002 | Lee et al. |
| 6,476,057 B1 | 11/2002 | Sikorski et al. |
| 6,476,075 B1 | 11/2002 | Sikorski et al. |
| 6,479,434 B1 | 11/2002 | Gillespie et al. |
| 6,479,552 B2 | 11/2002 | Sikorski et al. |
| 6,486,096 B1 | 11/2002 | Hacker et al. |
| 6,491,903 B1 | 12/2002 | Forster et al. |
| 6,498,125 B2 | 12/2002 | Edmunds et al. |
| 6,518,429 B2 | 2/2003 | Lee et al. |
| 6,521,607 B1 | 2/2003 | Sikorski et al. |
| 6,534,077 B2 | 3/2003 | Policelli et al. |
| 6,534,445 B1 | 3/2003 | Edmunds et al. |
| 6,544,974 B2 | 4/2003 | Sikorski et al. |

| | | |
|---|---|---|
| 6,552,187 B1 | 4/2003 | Maetzke |
| 6,555,499 B1 | 4/2003 | Glock et al. |
| 6,562,760 B1 | 5/2003 | Feucht et al. |
| 6,583,183 B2 | 6/2003 | Sikorski et al. |
| 6,586,433 B2 | 7/2003 | Silorski et al. |
| 6,593,274 B2 | 7/2003 | Policello |
| 6,605,568 B1 | 8/2003 | Massmann et al. |
| 6,624,180 B2 | 9/2003 | South et al. |

FOREIGN PATENT DOCUMENTS

| | | |
|---|---|---|
| DE | 32 48 554 | 7/1983 |
| DE | 32 19 490 | 12/1983 |
| DE | 32 30 087 | 2/1984 |
| DE | 32 39 071 | 4/1984 |
| DE | 33 40 265 | 5/1985 |
| DE | 36 31 071 | 3/1988 |
| DE | 42 33 333 | 4/1994 |
| EP | 0 104 876 | 9/1983 |
| EP | 0 107 156 | 10/1983 |
| EP | 0 224 078 | 11/1986 |
| EP | 0 292 122 | 4/1988 |
| EP | 0 524 525 | 7/1992 |
| EP | 0 708 082 | 10/1995 |
| FR | 2 518 990 | 10/1982 |
| GB | 2 090 246 | 7/1982 |
| JP | 58-116450 | 7/1983 |
| JP | 59-67265 | 4/1984 |
| JP | 59-155353 | 9/1984 |
| WO | WO 89/10922 | 11/1989 |
| WO | WO 95/04032 | 2/1995 |
| WO | WO 95 18788 | 7/1995 |

OTHER PUBLICATIONS

Hawley's Condensed Chemical Dictionary 13th edition, revised by Richard J. Lewis, 1997, Van Nostrand Reinhold, NY, p. 291.*

XP-002323969 J. Org. Chem. 18 1999, 64, 6528-6529.

* cited by examiner

CPHA Process Flow Diagram
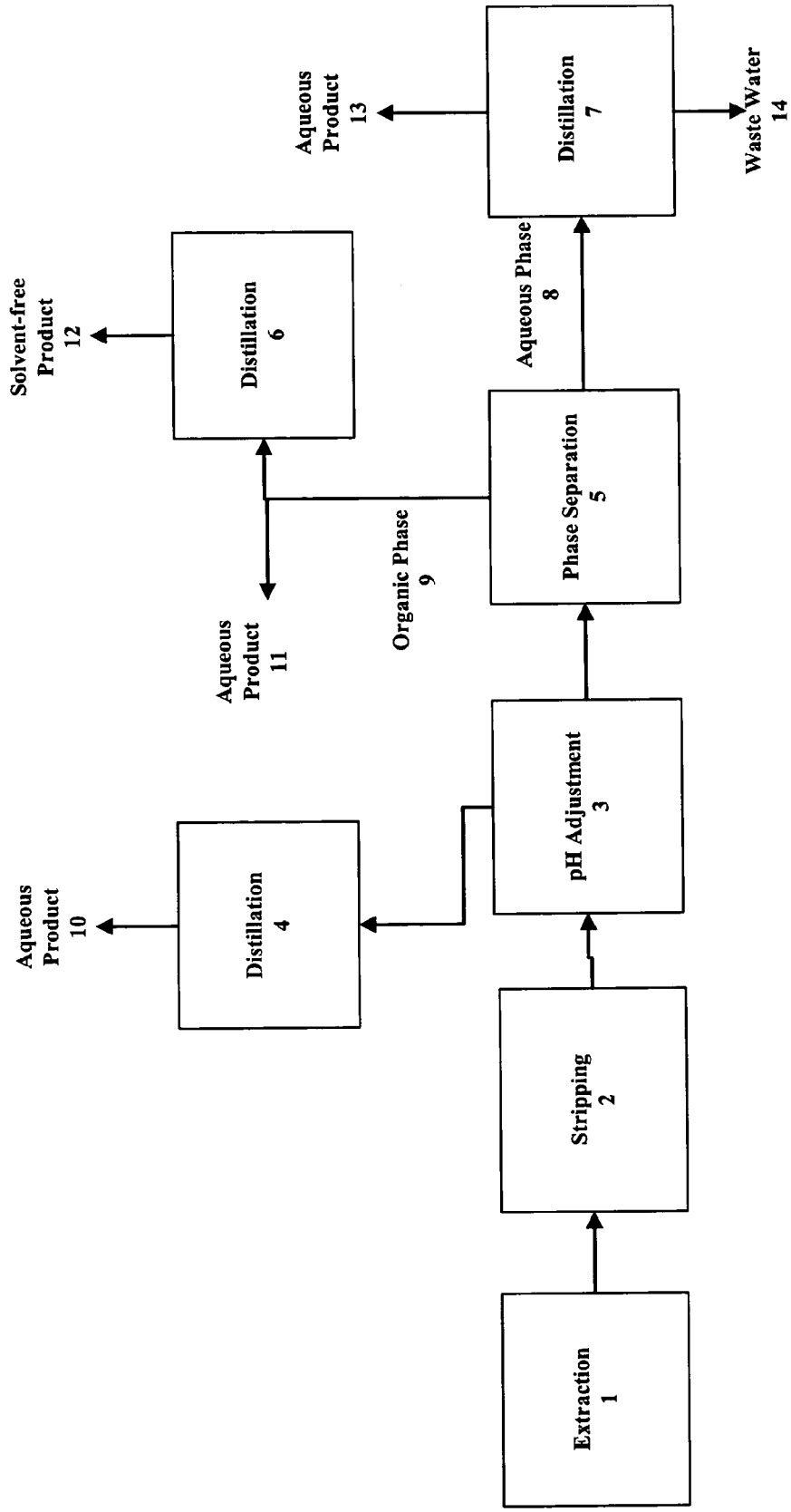

O-(3-CHLOROPROPENYL) HYDROXYLAMINE FREE BASE

BACKGROUND OF THE INVENTION

1. Field of the Invention

The present invention relates generally to a unique O-substituted hydroxylamine free base. More particularly, the O-substituted hydroxylamine preferably exhibits at least one property selected from the group consisting of: essentially free of hydroxylamine; essentially free of any solvents; a purity above 98% by gas chromatographic area; a water content of between about 0% to 90% by weight; and a high strength (as measured by mole of the O-substituted hydroxylamine per gram of sample) of between about 0.5 to 3.3-fold as much as a 40% O-substituted hydroxylamine salt solution, by weight. The O-substituted hydroxylamine free base is particularly useful in forming an herbicidal composition which can be used for controlling the growth of vegetation.

2. Discussion of the Background Art

O-(3-Chloro-2-propenyl)hydroxylamine (CPHA), especially trans-isomer, or its salts is an important intermediate for a number of herbicides. This compound has always been prepared in its salt form, especially its hydrochloride (CPHA-HCl). One concern is that the CPHA salts contain significant amount of hydroxylamine, which is more reactive with ketones or aldehydes to form undesirable impurities. Some of these impurities are restricted by the United States Environmental Protection Agency (EPA). Another concern is that CPHA-HCl salt solution is unstable. Refrigeration is always required to maintain temperature below at least 15° C., otherwise substantial decomposition occurs. For example, the commercially available 40% CPHA-HCl solution decomposes by more than half (e.g., 52%) after 23 days at 35° C. Further more, CPHA salts have a limited solubility in water. The practical concentration is about 40%, which is close to its saturation. This limited concentration results in not only a lot of transportation of water, but a lot of brine waste generated in the neutralization step in their application as well. Besides hydroxylamine, there are a number of other significant impurities in the solutions of CPHA salts. Some of them may compete with CPHA in the reactions to form new impurities. The users may suffer a yield penalty.

Commercially available 40% CPHA-HCL solutions have the following deficiencies: (a) contain about 1000 ppm hydroxylamine which reduces oximation yield, but are constrained by regulatory permits as well; (b) contain 0.5 equivalents of hydrochloric acid, which generates a large waste stream during commercial applications; (c) limited to applications where water presence is tolerated; (d) maximum solubility is about 45%, leaving a lot of transportation of water; (e) maximum feasibility concentration is 40%; and (f) contain 2–3% by weight of organic impurities, which may be carried over to end-products or generate new impurities in their applications.

O-substituted hydroxylamine salts can be prepared by oximation of a carbonyl compound, such as acetone, benzaldehyde, 2-butanone with hydroxylamine sulfate or hydrochloride in the presence of sodium hydroxide, followed by alkylation with an alkylating agent that bears the desired functional group. The alkylated oxime is then subject to hydrolysis catalyzed by an acid to form O-substituted hydroxylamine salt. In particular, the O-substituted hydroxylamine relevant to this invention is O-(3-chloro-2-propenyl)hydroxylamine. The preferred acid is hydrochloric acid. The obtained O-(3-chloro-2-propenyl)hydroxylamine hydrochloride (CPHA-HCl) in the art usually contains a number of significant impurities, including hydroxylamine in the range from 300 to 1500 ppm (parts per million) or about 0.33 to 1.64 mole %. Most of these impurities, especially hydroxylamine, have a significantly negative affect in the applications.

O-alkylhydroxylamines in their salt form have been prepared by reacting oximes with alkyl halides under basic conditions to give O-alkyl oximes, followed by acid catalyzed hydrolysis of the O-alkyl oxime. For example, PCT Application WO 8911473 discloses a process for producing O-substituted oxime compounds in which a large excess of propanone oxime in toluene is reacted with an aqueous alkali metal hydroxide to give, after azeotropic distillation, the oxime salt which on reaction with an alkyl halide followed by further distillation, acidification and extraction with toluene affords the O-alkyl oxime in moderate purity (83.5%). European Pat. No. 85-103052 discloses a similar process for the synthesis of O-alkyl oximes which were subsequently hydrolyzed using aqueous hydrochloric acid to give the O-alkylhydroxylamines.

Jap. Pat. No. 03258757 discloses a process in which acetone oxime is reacted with sodium hydride in N,N-dimethylformamide at 60° to 70° C. and the resulting oxime salt subsequently reacted with an alkyl bromide to give a low yield (37%) of an O-alkyl acetone oxime. Jap. Pat. No. 83-68791 discloses a similar process in which the acetone oxime salt is generated below 10° C. and subsequently reacted with a solution of an alkyl halide in dimethoxyethane to give a low yield (52.4%) of an O-alkyl oxime.

German Pat. No. 86-3631071 discloses a procedure for the preparation of O-substituted hydroxylamine hydrochlorides in which an O-alkyl acetone oxime, present in a mixture of 1,4-dioxane, water and hydrochloric acid, is hydrolyzed and the acetone continuously removed by distillation through a bubble tray column.

U.S. Pat. No. 5,488,162 discloses a process for preparing aqueous solutions of O-alkylhydroxylamine salts. The process involves converting hydroxylamine salts to their O-alkyl derivatives without the isolation of intermediates. More specifically, the process involves three steps. The first step, Step (A), involves forming a ketoxime. The second step, Step (B), involves adding an alkylating agent to the ketoxime formed in Step (A). The third step, Step (C), involves hydrolyzing the alkylated ketoxime formed in Step (B) to yield an O-alkylhydroxylamine salt. O-alkylhydroxylamine salts are important intermediates in the preparation of herbicides.

U.S. Pat. No. 5,557,013 demonstrates the preparation of O-substituted hydroxylammonium salts of the following formula:

$$H_2NOR_xHX$$

where R is a $C_1$–$C_6$-alkyl or $C_2$–$C_6$-alkenyl radical, each of which may be halogen-substituted, and X is chlorine or bromine, by reacting in an integrated process, without isolation of intermediates. The reaction steps include (a) reacting acetone with hydroxylammonium sulfate and sodium hydroxide solution to give acetone oxime; (b) treating the solution of acetone oxime thus obtained with sodium hydroxide solution and completely removing water; (c) reacting the suspension of the acetone oxime Na salt thus obtained with alkylating agents at from 0.5 to 15 bar and at up to 140° C. to give acetone oxime ethers; and (d) cleaving the acetone oxime ethers with acids HX to give the products I, a homogeneous, nonpolar aprotic solvent being used in all process steps (a) to (d).

Yet another conventional process is described in U.S. Pat. No. 5,585,520 for the preparation of O-substituted hydroxylammonium salts having the following formula:

$$R^1\text{—CHX—O—NH}_2.HL$$

(L=halogen, hydrogensulfate; X=H, alkyl; $R^1$=unsubstituted or substituted phenyl, thienyl, furanyl, pyrrolyl or —$CR^2$=$CR^3R^4$; $R^2$, $R^3$, $R^4$=H, halogen or alkyl) by reaction of an acetone oxime O-allyl or —O— benzyl ether of the following formula:

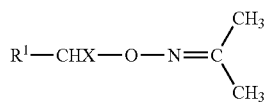

with water and a mineral acid H-L with continuous removal of the acetone formed in this process, by carrying out the hydrolysis batchwise at 0°–50° C. and under a pressure of 10–500 mbar.

Neither preparation nor applications of solvent-free CPHA free base or aqueous CPHA solution has been reported in the prior art. It has been unexpectedly found by the present inventors that CPHA free base according to the present invention is much more stable than its salt solutions. For example, a commercial 40% CPHA-HCl solution decomposes by 52% after 23 days at 35° C., whereas, a 85% CPHA aqueous solution has only 1.1% purity drop after 78 days at 40° C. Unlike CPHA-HCl product, which requires a refrigerated warehouse and refrigerated transportation, free base CPHA according to the present invention does not need refrigeration unless the storage time is over six months or the ambient temperature continuously exceeds 45° C.

The free base CPHA produced by the methods described in the present invention provides a superior quality. It is essentially free of hydroxylamine. It can also be essentially free of those impurities existing in the CPHA salts produced via the conventional processes discussed above. The term "essentially free of" as used herein means that those impurities become non-detectable by gas chromatography (GC), e.g., weigh 1.81 g of 51% by weight of CPHA free base aqueous solution in a vial containing 2.18 g of cyclohexanone; stir the mixture in the capped vial at 50° C. for 2 hours; after cooling, add 8.0 g of dichloromethane and shake for one minute; settle for 5 minutes; gas chromatographic (GC) analysis of the organic phase indicates 0.00% area for cyclohexanone oxime, which indicates that there is no hydroxylamine in the sample.

Free base CPHA is miscible with water at room temperature, hence one can produce any concentration of CPHA from very dilute to near 100% based on the present invention. The preferred free base CPHA concentration of the present invention is between about 50–55%, by weight, which has about 70–80% more strength than the conventional 40% CPHA-HCl solution. A 99% purity of solvent-free CPHA of the present invention is about 3.3 times as effective as 40% CPHA-HCl solution.

A high purity CPHA produced via the present invention is superior in pharmaceutical applications, where even a 0.1% level impurity can affect the process significantly. One can also produce a free base CPHA solution in any suitable solvents for customized applications based on the present invention. This is extremely important for pharmaceutical and agricultural applications because hydroxylamine is more reactive than CPHA, thereby reducing yield and generating undesirable impurities. Moreover, the aqueous free base CPHA according to the present invention has no inorganic substances and is therefore particularly useful for pharmaceutical and agricultural applications. Finally, the solvent-free CPHA free base according to the present invention can have a concentration of 100% or less, thus one pound of 100% CPHA free base is equivalent to 3.35 pounds of conventional 40% CPHA-HCl salt solution.

SUMMARY OF THE INVENTION

An O-substituted hydroxylamine having the following general formula:

$$R^1\text{—CHX—O—NH}_2$$

wherein X is hydrogen or an alkyl; and $R^1$ is an unsubstituted or substituted phenyl, thienyl, furanyl, pyrrolyl or —$CR^2$=$CR^3R^4$; wherein $R^2$, $R^3$ and $R^4$ are hydrogen, halogen or alkyl. The O-substituted hydroxylamine exhibits at least one property selected from the group consisting of: essentially free of hydroxylamine (as measured by the method described in Example 1); essentially free of any solvent; a water content of between about 0% to 90% (as measured by Karl Fischer, Metrohm model 751 GPD Titrino); and a high strength (as measured by mole of the O-substituted hydroxylamine per gram of sample) of between about 0.5 to 3.3-fold as much as a 40% O-substituted hydroxylamine salt solution, by weight. The O-substituted hydroxylamine may further comprise at least one additional property selected from the group consisting of: a purity of between about 98% to 100%, based on gas chromatographic area described in Example 1; and a purity drop of less than about 1.2% after 78 days at 40° C. when the O-substituted hydroxylamine has a concentration of about 85% in water, based on gas chromatographic area described in Example 1. The O-substituted hydroxylamine is at least one isomer selected from the group consisting of cis, trans and a mixture thereof.

The O-substituted hydroxylamine is preferably trans-O-(3-chloro-2-propenyl)hydroxylamine and/or the mixture of trans-& cis-O-(3-chloro-2-propenyl)hydroxylamine, and is preferably formed by the following steps comprising: (a) optionally admixing an organic solvent with an O-substituted hydroxylamine salt (e.g., O-(3-chloro-2-propenyl)hydroxylamine hydrochloride) solution, and extracting impurities from the aqueous phase at a certain pH and the post extraction phase separation; (b) optionally stripping residual organics from the aqueous phase to form an aqueous-enriched phase; (c) adjusting the pH of the aqueous-enriched phase to a pH of at least about 3.5, thereby forming an organic-enriched stream and an aqueous phase stream; and (d) isolating product from either or both the organic-enriched stream and the aqueous phase stream.

The organic solvent used in extraction step (a) is preferably, one solvent selected from, but not limited to, the group consisting of: aliphatic compounds (such as alkanes, alkenes, halides, ethers, alcohols, esters, nitriles, and nitrocompounds), alicyclic compounds, and aromatic compounds (such as benzene, alkylated benzene, alkoxybenzene, nitrobenzene, and phenyl halides). The preferred solvents are 1,3-dichloropropene, 1,3-dichloropropane, and O-(3-chloro-2-propenyl)acetoxime.

The pH value during extraction step (a) is preferably about 7 or less, more preferably less than about 4. The temperature during extracting step (a) is generally between about 97° C. and the freezing point of the O-substituted hydroxylamine salt solution. The pressure during extracting step (a) is preferably between about 0.05 to 15 atmospheric pressure. The post-extraction phase separation step (a) operates under the same pH, temperature and pressure as set forth above regarding the extraction. Most preferably, the pH is maintained below about 3.5, the temperature is maintained between about −10° C. to 97° C., and the pressure is maintained from about 0.5 to 1.5 atmospheric pressure.

In the solvent stripping step (b) organic solvent is completely removed by distillation, either simple distillation (without a column) or fractional distillation. Fractional distillation is preferred. The most preferred distilling column has about 5–15 theoretical plates. The distillation can be done either under pressure or under vacuum, depending on the nature of the solvent used in the extraction step (a). The preferred pressure ranges from about 5 to 800 torr. The most preferred pressure is between about 10 to 150 torr. The preferred pH range is the same as set forth above regarding the extraction.

In the pH adjustment step (c) O-substituted hydroxylamine is released at pH above about 3.5. A pH range between about 4.5 to 13 is preferred. The pH adjustment step (c) is operated under any pressure and at a temperature range from about −10 to 97° C. The preferred pressure is between about 0.5 to 1.5 atmospheric pressure. A temperature range from about 0 to 60° C. is most preferred.

The product isolation step (d) comprises at least one of the following steps: (i) separating the organic-enriched stream from the aqueous phase stream, wherein the organic-enriched stream is the O-substituted hydroxylamine in water; (ii) distilling the aqueous stream, wherein the overhead is the O-substituted hydroxylamine in water; (iii) optionally, distilling the entire two-phase stream from the pH adjustment step (c), wherein the overhead is the O-substituted hydroxylamine in water; and (iv) optionally, fractionally distilling the organic-enriched stream, wherein the overhead after a precut is essentially solvent-free O-substituted hydroxylamine.

The distilling operations in steps (d)(ii) and (d)(iii) are conducted via distillation. The distillation unit preferably comprises at least a column, a condenser, a reflux ratio controller, and a receiver. The column preferably comprises about 0–35 theoretical plates, more preferably between about 5–15 theoretical plates. The pressure during the distilling steps (b), (d)(ii) and (d)(iii) is preferably between about 5 to 800 torr. Optionally, water may be added periodically during the stripping steps mentioned above. Fractional distillation is preferred for distilling step (d)(iv), wherein the organic-enriched stream is distilled to produce solvent-free O-substituted hydroxylamine free base. A column equivalent to about 5–35 theoretical plates is preferred. However, a column with about 0–5 theoretical plates can still provide essentially solvent-free O-substituted hydroxylamine product with less efficiency. A column with more than about 35 theoretical plate can make the fractional distillation more efficient, but more costly. Any other separation techniques now known or to be developed by those of ordinary skill in the art are also contemplated by the present invention.

A herbicidal composition formed from the reaction product of: a trione intermediate having the general formula:

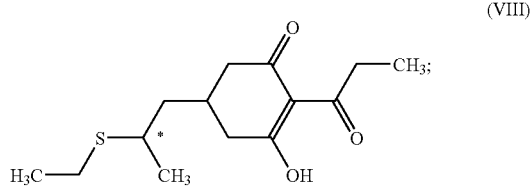

and an O-substituted hydroxylamine having the following general formula:

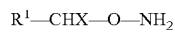

wherein X is hydrogen or an alkyl; and $R^1$ is an unsubstituted or substituted phenyl, thienyl, furanyl, pyrrolyl or $-CR^2=CR^3R^4$; wherein $R^2$, $R^3$ and $R^4$ are hydrogen, halogen or alkyl. and the O-substituted hydroxylamine is essentially free of hydroxylamine (as measured based on the method described in Example 1).

The herbicidal composition further comprises at least one additive selected from the group consisting of: crop oil concentrates, surfactants, fertilizers, emulsifiers, dispersing agents, foaming activators, foam suppressants, and correctives. Optionally, the herbicidal composition further comprises an inert carrier and/or at least one other biologically active chemical.

A method for controlling growth of vegetation comprising: applying to said vegetation a herbicidal composition formed from the reaction product of: a trione intermediate having the general formula:

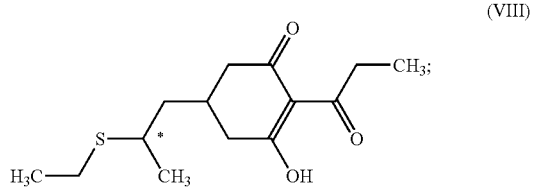

and an O-substituted hydroxylamine having the following general formula:

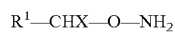

wherein X is hydrogen or an alkyl; and $R^1$ is an unsubstituted or substituted phenyl, thienyl, furanyl, pyrrolyl or $-CR^2=CR^3R^4$; wherein $R^2$, $R^3$ and $R^4$ are hydrogen, halogen or alkyl, in a herbicidally effective amount.

The present invention also includes an O-substituted hydroxylamine salt having the following general formula:

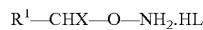

wherein L is a halogen or hydrogensulfate; X is hydrogen or alkyl; $R^1$ is unsubstituted or substituted phenyl, thienyl, furanyl, pyrrolyl or $-CR^2=CR^3R^4$; wherein $R^2$, $R^3$, and $R^4$ are each hydrogen, halogen or alkyl; and wherein the O-substituted hydroxylamine salt is essentially free of hydroxylamine.

The O-substituted hydroxylamine salt is preferably formed by the following steps comprising:
  a. optionally admixing an organic solvent with an O-substituted hydroxylamine salt solution to form at least an aqueous phase and extracting impurities from the aqueous phase;

b. optionally stripping residual organic solvents from the aqueous phase to form an aqueous-enriched phase;

c. adjusting the pH of the aqueous-enriched phase to a pH of at least about 3.5, thereby forming an organic-enriched stream and an aqueous phase stream;

d. separating the O-substituted hydroxylamine from the organic-enriched stream and/or the aqueous phase stream; and e. reacidifying the O-substituted hydroxylamine, thereby forming the O-substituted hydroxylamine salt which is essentially free of hydroxylamine.

BRIEF DESCRIPTION OF THE DRAWINGS

FIG. 1 is a schematic flow chart of the CPHA free base process according to the present invention.

DETAILED DESCRIPTION OF THE PREFERRED EMBODIMENT

The present invention provides a unique free base CPHA product and a unique method to produce such hydroxylamine-free O-(3-chloro-2-propenyl)hydroxylamine (CPHA) or its salts, e.g. O-(3-chloro-2-propenyl)hydroxylamine hydrochloride (CPHA-HCl), if it is desired. The present invention also provides a method to produce O-(3-chloro-2-propenyl)hydroxylamine or its salts with non-detectable impurities.

The process described in the present invention comprises at least one of the following steps. These steps include (a) extraction, (b) stripping, (c) free-base release or pH adjustment, and (d) distillation (i.e., product isolation). All these steps can be performed with or without the atmosphere of an inert gas. The process can best be described by reference to FIG. 1.

In extraction step 1, an organic solvent is used to stir and equilibrate with a solution of O-(3-chloro-2-propenyl)hydroxylamine salt (e.g., Hocal●HCl manufactured by Honeywell International Corporation, Morristown, N.J.). The preferred solvents are, but not limited to, 1,3-dichloropropene, 1,3-dichloropropane, and O-(3-chloro-2-propenyl) acetoxime. The extraction is accomplished at about pH 7 or below, preferably below about pH 4. The temperature for extraction is controlled generally between about −10 to 97° C. depending on the composition and concentration. The preferred temperature is below about 60° C. The extraction can be performed under any pressure. The most preferred pressure is generally between about 0.5 to 1.5 atmospheric pressure. In most cases, the extraction is done under atmospheric pressure. After extraction, the mixture is settled for post extraction phase separation. The phase separation is performed under the conditions of pH, temperature, and pressure with the same range as described for extraction. After phase disengagement, the aqueous phase is taken to next step.

The stripping step 2 involves transferring an aqueous stream from phase separation to a still equipped with at least a column, a condenser, a reflux ratio controller, and a receiver. Any type of column can be used. The column is preferably, but not limited to, equivalent to about 0–35 theoretical plates. The most preferred column has about 5–15 theoretical plates. The still can be heated by any means. However, steam heating is preferred. The strip is performed either under pressure or under vacuum depending on what solvent is used in the extraction step. The preferred pressure is between about 10 to 200 torr. Additional water may be needed before or during the strip because of water loss during the distillation. The stripping is continued until there is no organic substances coming out to the distillate. The aqueous stream in the still is then transferred to a vessel or stays in the still for next step.

The above two steps 1 and 2 can sometimes be skipped only if the starting material, CPHA-HCl solution, contains organic impurities at a tolerable level for a particular application.

The next step 3 is free-base release. In this step 3, the aqueous solution is adjusted to a pH value above about 3.5 by introducing a base. The useful bases are, but not limited to, sodium hydroxide, potassium hydroxide, sodium carbonate, potassium carbonate, sodium bicarbonate, potassium bicarbonate, sodium acetate, and potassium acetate. The most preferred base is sodium hydroxide. The desired pH range is from about pH 3.5 to pH 14. A pH range between about 4.5 and 13 is preferred. A pH range from about 6.5 to 13 is most preferred. This step 3 can be operated under any pressure and at a temperature range from freezing point to boiling point. The most preferred temperature range is between about 0° C. to 60° C. Atmospheric pressure is most preferred.

After pH adjustment, two phases are formed, organic-rich phase 9 and aqueous phase 8. There are two options to this two-phase system. The first option is to send this two-phase mixture directly to distillation unit 4 in either continuous manner or batch operation step 4, thereby taking as overhead from distillation unit 4 an aqueous O-substituted hydroxylamine product 10 according to the present invention. If this option is selected, a product 10 with a concentration below about 32% can be directly obtained from distillation step 4. The second option is to do phase separation to give organic phase 9 and aqueous phase 8. Organic phase 9 is an O-substituted hydroxylamine product with a concentration of between about 82–88%, the balance being water. From this organic phase 9, a solvent-free CPHA product 12 according to the present invention with up to 100% purity of CPHA is obtained by distillation via distillation unit 6. Aqueous phase 8 is sent to distillation unit 7 equipped with at least a column, a condenser, a reflux ratio controller, and a receiver. Any type of column can be used. The preferred column has, but is not limited to, an equivalent to about 0–35 theoretical plates. The most preferred column has about 5–15 theoretical plates. The still can be heated by any means. However, steam heating is preferred. The distillation in distilling unit 7 is performed either under pressure or under vacuum. It is preferred that the distillation is performed under a reduced pressure. The preferred pressure is between about 5 to 800 torr. The most preferred pressure is between about 10 to 150 torr. Thereafter, a waste water stream 14 is removed as bottoms from distillation unit 7 and an aqueous CPHA product stream 13 according to the present invention is taken overhead.

The O-substituted hydroxylamine salt is preferably formed by the following steps comprising:

a. optionally admixing an organic solvent with an O-substituted hydroxylamine salt solution to form at least an aqueous phase and extracting impurities from the aqueous phase;

b. optionally stripping residual organic solvents from the aqueous phase to form an aqueous-enriched phase;

c. adjusting the pH of the aqueous-enriched phase to a pH of at least about 3.5, thereby forming an organic-enriched stream and an aqueous phase stream;

d. separating the O-substituted hydroxylamine from the organic-enriched stream and/or the aqueous phase stream; and e. reacidifying the O-substituted hydroxylamine, thereby forming the O-substituted hydroxylamine salt which is essentially free of hydroxylamine.

Set forth in the below chart are the various process steps according to the present invention and their respective operating parameter ranges.

| | Step | Parameter | Range | Preferred Range |
|---|---|---|---|---|
| A | Extraction Step | pH | Below 7 | Below 4 |
| | | Temperature | −10 to 97° C. | 0 to 60° C. |
| | | Pressure | 0 to 15 atm | 0.5 to 1.5 atm |
| B | Stripping Step | pH | Below 7 | Below 4 |
| | | Pressure | 5 to 800 torr | 10 to 150 torr |
| | | Column | 0 to 35 theoretical plates | 5 to 15 theoretical plates |
| c | pH Adjustment Step | pH | 3.5 to 14 | 4.5 to 13 |
| | | Temperature | −10 to 97° C. | 0 to 60° C. |
| | | Pressure | 0 to 15 atm | 0.5 to 1.5 atm |
| d | Product Isolation Step | | | |
| (d)/(i) | Separating organic Phase | pH | 3.5 to 14 | 4.5 to 13 |
| | | Temperature | −10 to 97° C. | 0 to 60° C. |
| | | Pressure | 0 to 15 atm | 0.5 to 1.5 atm |
| (d)/(ii) | Distilling Aqueous Stream | pH | 3.5 to 14 | 4.5 to 13 |
| | | Pressure | 5 to 800 torr | 10 to 150 torr |
| | | Column | 0 to 35 theoretical plates | 5 to 15 theoretical plates |
| (d)/(iii) | Distilling Two-phase Stream | pH | 3.5 to 14 | 4.5 to 13 |
| | | Pressure | 5 to 800 torr | 10 to 150 torr |
| | | Column | 0 to 35 theoretical plates | 5 to 15 theoretical plates |
| (d)/(iv) | Distilling Organic-enriched Stream | Pressure | Reduced pressure | 0–100 torr |
| | | Column | 0 to 35 theoretical plates | 5 to 15 theoretical plates |

Undesired vegetative growth in an agricultural setting can greatly impact the ultimate yield of crop plants. More commonly referred to as weeds, such growth can deplete the available water and nutrients available to desired plants, thereby inhibiting the growth of the desired plant and reducing the yield of useful plant materials. The use of herbicides to control plant growth has proven to be a successful means of countering the deleterious effects that weeds may have on crop growth.

Certain cyclohexanedione oximes are known in the art as having excellent herbicidal activity against a variety of post-emergent grasses in a variety of environments. Examples of cyclohexanedione oximes include clethodim, sethoxydim, cycloxydim, alloxydim, tralkoxydim, tepraloxydim, and clefoxydim. These compounds are characterized by a single ring structure that involves keto functions in the 1 and 3 positions with an oxime function in the 2 position. The significance of the structural similarity is revealed in the mode of action of these compounds, which involves chelation of metal ions associated with plant enzymes, otherwise responsible for promoting necessary biochemical reactions in the plant. This binding effect involves the oxime side chain and the enolic form of the 1,3-diketone to form a six-member ring incorporating the metal ion.

The 5 position substitutions of three of the cyclohexanedione oximes, clethodim, sethoxydim, and cycloxydim, contains a chiral carbon atom. As with many organic compounds, these three cyclohexanedione oximes exist in optically active forms, i.e., they have the ability to rotate the plane of plane-polarized light. In describing an optically active compound, the prefixes d and l or s and r are used to denote the absolute configuration of the molecule about its chiral center(s). The prefixes d and l, or (+) and (−) respectively, are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such enantiomers is often called an enantiomeric or racemic mixture. Enhanced activity of a single enantiomer, over that of a racemic mixture and the other opposite enantiomer, has not been taught or suggested based on studied modes of action of these compounds.

Clethodim and related compounds are described in U.S. Pat. Nos. 4,440,566 and 6,300,281, which are incorporated herein by reference. The generic chemical structure of clethodim is shown below in formula I:

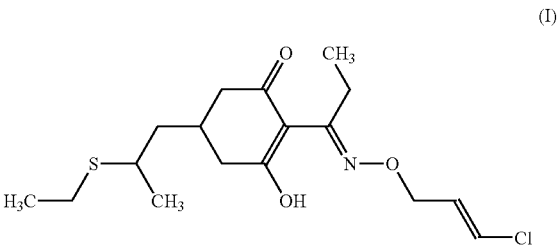

(I)

Clethodim (generic name), or Select® (trade name) (Valent U.S.A. Corp.), is a particularly important commercial herbicide within the class of cyclohexanedione oximes characterized by a 5 position substitution. It is generally systematically applied to crop plants, such as soybeans, so that the growth of grass weeds growing in the plot can be controlled. Select® is commercially produced as a composition comprising 26.4% clethodim by weight and 73.6% other ingredients, referred to as Select® 2EC (Valent U.S.A. Corp.), reflecting that it contains 2 pounds active ingredient (clethodim) per gallon.

While many effective herbicides, such as clethodim, have been developed, those skilled in the art will recognize that there is a need for herbicides with greater selectivity and improved effectiveness over current compounds. Use of such improved herbicides will result in decreased damage to non-target plants and reduced application rates, thereby reducing environmental effects and costs. This invention is directed to these, and other important ends.

The presently available racemic mixture of clethodim (i.e., a 1:1 racemic mixture of the two stereoisomers) is a selective post-emergence herbicide for control of annual and perennial grasses in and around soybeans, cotton, sugar beets, onions (dry bulb only), garlic, shallots (dry bulb only), tomatoes, alfalfa, peanuts, dry beans, and non-bearing food crops.

(−) clethodim has increased potency compared to the racemic form or (+) clethodim when used in a herbicidal composition comprising a herbicidally-effective amount of (−) clethodim.

Optically pure (−) clethodim means the (−) or l isomer of clethodim synthesized by one of the methods described herein, or isolated in substantially optically pure form from the racemic mixture. "Substantially optically pure" form of the active compound, as used herein, means that the desired isomer is synthesized or isolated at 98–100%, preferably 100%, purity relative to the other optical isomer.

With respect to the term "substantially free of" as used herein means that the composition contains a greater proportion or percentage of the (−) or 1 enantiomer of clethodim, on a weight basis, in relation to the (+) or d enantiomer of clethodim, these percentages being based on the total amount of clethodim optical isomers present. In a preferred embodiment, the term "substantially free of" as used herein means that the composition contains at least 60% by weight of (−) or 1 clethodim enantiomer, and 40% by weight or less of the (+) or d enantiomer. In a more preferred embodiment, the term "substantially free of" means that the composition contains at least 75% by weight of (−) or 1 clethodim enantiomer, and 25% or less of the (+) or d enantiomer. In a still more preferred embodiment, the term "substantially free of" means that the composition contains at least 90% by weight of (−) or 1 clethodim enantiomer, and 10% or less of the (+) or d enantiomer. In an even more preferred embodiment, the term "substantially free of" means that the composition contains at least 99% by weight of (−) or 1 clethodim enantiomer, and 1% or less of the (+) or d enantiomer. In the most preferred embodiment, the term "substantially free of" means that the composition contains 100% by weight of (−) or 1 clethodim enantiomer, and none of the (+) or d enantiomer, again based on the total amount of clethodim.

In certain preferred embodiments, the amount of (−) clethodim present in a desired composition is "herbicidally-effective." As used herein, the term "herbicide" means that a compound or composition negatively controls or modifies the growth of plants. Such controlling or modifying effects can include all deviations from natural development, such as killing, growth retardation, defoliation, desiccation, regulation, stunting, tillering, leaf bum, dwarfing, and the like. The term "herbicidally-effective amount" is meant to include any amount of such compound or composition which causes such negative modifying effect upon the growth of plants. Preferred application rates on a per acre basis are discussed below. The term "herbicidal composition" is meant to include compounds comprised of (−) clethodim substantially free of (+) clethodim which causes such negative modifying effect upon the growth of plants. The term "controlling" is meant to include all deviations from natural plant development, such as killing, growth retardation, defoliation, desiccation, regulation, stunting, tillering, leaf bum, dwarfing, and the like.

It will be recognized by those skilled in the art that certain herbicidal compositions are more effective in controlling the growth of plants at one stage or another. It will further be recognized by those skilled in the art that certain herbicidal compositions are more effective in controlling the growth of one plant species or another. Thus, it is within the purview of one skilled in the art to recognize or determine the stage and/or species for which application of a particular growth regulating composition is most suitable.

It is generally desirable that a growth regulating composition used against undesired plant species destroy or prevent the growth of as much of an undesired plant species as feasible, such as, for example, by destroying at least about 80% of an established undesired plant. However, it will be recognized by those skilled in the art that suppression or destruction of plant growth at lower levels, particularly with some noxious and/or herbicide-resistant plants, can be commercially advantageous.

These methods and compositions are useful in inhibiting or controlling the growth of plant species, including annual weeds. Preferably, the active compound of the present invention is differentially herbicidally active toward at least one desired plant species. By "differentially herbicidally active" is meant that the active compound may display less herbicidal activity toward a particular desired plant species as compared to their activity against one or more undesired plant species. In still more preferred embodiments, the methods and compositions of the present invention are substantially herbicidally inactive toward at least one desirable plant species. By "substantially inactive" is meant that the composition causes less than 20% damage to desired plant species. Such desirable plants are generally referred to as "crop plants." The term "crop plants," as used herein, includes any edible or non-edible, including decorative, plant species with commercial value, which is planted and cultivated for commercial use. Thus, crop plants include floral plants, trees, vegetable plants, and the like. The term "plants" is meant to include germinant seeds, emerging seedlings and established vegetation, including roots and above-ground portions.

Grass plants can be controlled using the compositions and methods of the present invention. Preferably, the grass plant to be controlled is in a post-emergent growth stage at the time of application of the herbicidal compositions of this invention. Examples of grass plant species against which the compositions and methods of the present invention are effective include, but are not limited to, the following:

| Annual grasses | |
|---|---|
| Barnyardgrass | *Echinochloa crus-galli* |
| Broadleaf Signalgrass | *Brachiaria platphylla* |
| Bromes | *Bromus* species |
| Crabgrasses | *Digitaria* species |
| Crowfootgrass | *Dactyloctenium aegyptium* |
| Fall Panicum | *Panicum dichotomiflorum* |
| Foxtails | *Setaria* species |
| Goosegrass | *Eleusine indica* |
| Itchgrass | *Rottboellia exaltata* |
| Junglerice | *Echinochloa colona* |
| Lovegrass (Stinkgrass) | *Eragrostis cilanensis* |
| Red Rice | *Oryza sativa* |
| Rygrasses | *Lolium* species |
| Seedling Johnsongrass | *Sorghum halepense* |
| Shattercane | *Sorghum bicolor* |
| Southwestern Cupgrass | *Eriochloa gracillis* |
| Sprangetops | *Leptochloa* species |
| Texas Panicum | *Panicum texanum* |
| Volunteer | |
| Barley | *Hordeum vulgare* |
| Oats | *Avena sativa* |
| Rye | *Secale cereale* |
| Wheat | *Triticum aestivum* |
| Corn | *Zea mays* |
| Grain Sorghum | *Sorghum bicolor* |
| Wild Oats | *Avena fatua* |
| Wild Proso Millet | *Panicum miliaceum* |
| Witchgrass | *Panicum capillare* |
| Woolly Cupgrass | *Eriochloa villosa* |
| Perennial grasses | |

-continued

| | |
|---|---|
| Bermudagrass | Cynodon dactylon |
| Fescue | Festuca arundinacea |
| Foxtail Barley | Hordeum jubatum |
| Orchardgrass | Dactylis glomerata |
| Quackgrass | Agropyron repens |
| Rhizome Johnsongrass | Sorghum halepense |
| Wirestem Muhly | Muhlenbergia frondisa |

Production of (−) Clethodim (−) Clethodim substantially free of (+) clethodim, as well as optically pure (−) clethodim, can be isolated from a racemic mixture of clethodim by preparative liquid chromatography using procedures well known to one of ordinary skill in the art. Racemic clethodim can be prepared as described in U.S. Pat. No. 4,440,566, incorporated by reference herein. Alternatively, (−) clethodim substantially free of (+) clethodim, as well as optically pure (−) clethodim, can be produced by the following method. The optically pure (−) clethodim is the (−) or 1 optical isomer of the two isomers encompassed by formula (II):

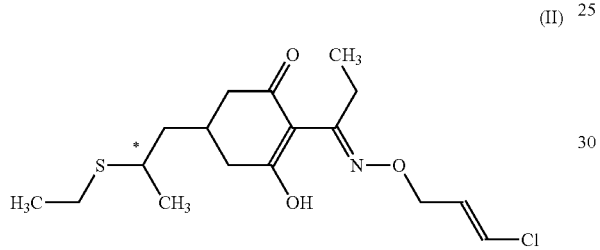

(II)

wherein the asterisk indicates the asymmetric or chiral carbon atom.

a) Preparation of 3-Ethylthiobutanal (−) Clethodim may be prepared by first reacting ethanethiol and crotonaldehyde (ca. equal molar amounts), in the presence of catalytic triethylamine (ca. 10 mole %), to yield 3-ethylthiobutanal (ETB) (formula III; the asterisk denotes the chiral center). The reaction is known to proceed spontaneously.

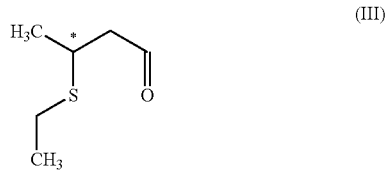

(III)

A refinement of crude ETB is performed by applying a vacuum to the crude ETB to remove contaminating water and ethanethiol. The resulting residue is taken up in diethyl ether and dried over sodium sulfate. The resulting filtrate is concentrated on a rotary evaporator and then maintained under high vacuum to yield an amber oil. Product identity in each step may be verified by NMR, and purity may be determined by gas chromatography (GC) area %.

b) Preparation of Racemic Aldol

A mixture of methyl acetoacetate and water is placed in a round bottom flask and blanketed with nitrogen. Sodium hydroxide is added (ca. equal molar amount), with external cooling to maintain the exotherm to less than 30° C. The resulting slurry is stirred at ambient temperature overnight. The pH is adjusted to approximately neutral by addition of concentrated hydrochloric acid. To this mixture is added methanol and triethylamine (ca. 10 mole %), followed by addition of 3-ethylthiobutanal (ca. equal molar amount). The resulting exotherm (ca. 5–10° C.) is allowed to proceed unchecked. Stirring is continued under heat for several hours, and then overnight at ambient temperature. Concentrated hydrochloric acid is added to obtain an acidic pH. The aqueous layer is separated, and extracted with diethyl ether. The diethyl ether extract is then combined with the organic layer. The combined organic layer is concentrated on a rotary evaporator, and then mixed with benzene. Residual water is removed as an azeotrope, and the remaining benzene is stripped. The residue is maintained under high vacuum to remove residual lights. An amber oil (the racemic aldol intermediate of formula IV) is obtained. Note that a second, transitory, chiral center is present in the structure specified in formula IV (denoted by .).

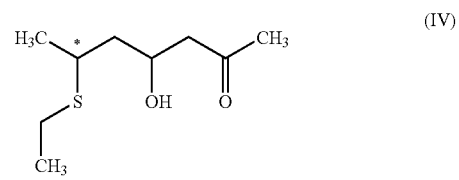

(IV)

c) Determination of Specific Rotations and Preparation of Chiral Aldol

A small portion of the racemic aldol intermediate is separated into its four enantiomers on a preparative HPLC column. The samples are treated with phosphoric acid, as described in the next section, to eliminate the second chiral center and allow unambiguous determination of specific rotations. The remainder of the racemic aldol is then processed through, and the appropriate peaks identified, allowing collection of the target (−)-enantiomer in the desired amount relative to the (+)-enantiomer. (+) Clethodim can also be made using this method, however, at this step the (+)-enantiomer would be collected and processed through the remainder of the steps, if desired.

The refinement of these separations determines the degree of optical purity. Optically pure enantiomers of 99–100% purity can be obtained through efficient separation. The optical purity of the clethodim isomer derived from these separated intermediates is the same as the intermediates themselves since no change in optical orientation is created by the additional reactions required to produce clethodim. Thus, optically pure enantiomers of 100% purity can be obtained under the described conditions. However, in practice, less than 100% optical purity is adequate to practice the principles of the invention, within the ranges defined above.

d) Preparation of Unsaturated Ketone

The (−) chiral aldol intermediate is mixed with phosphoric acid (ca. equal molar amounts) and benzene. The mixture is stirred under heat and then allowed to cool to ambient temperature. A sample of the organic layer is analyzed by GC to verify completion of the reaction. The aqueous layer is separated and discarded. The organic layer is washed with water and sodium bicarbonate, then dried over sodium sulfate, filtered, and stripped, producing formula V. The dehydration introduces a double bond and eliminates the second chiral center (see formula V).

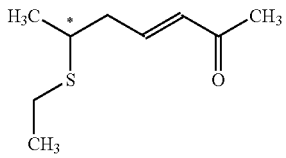
(V)

e) Dione Synthesis

Sodium methoxide (25% solution in methanol) is added to a mixture of the formula V intermediate and dimethyl malonate (ca. equal molar amounts), with cooling as required to sustain ambient temperature. The mixture is then stirred overnight at ambient temperature. Reaction completion is verified by thin layer chromatography. With external cooling, ice water is added, and then concentrated hydrochloric acid to obtain an acidic pH. The aqueous layer is separated and discarded. The organic layer is washed with brine, dried over sodium sulfate, filtered and concentrated on a rotary evaporator. The reaction product is formula VI.

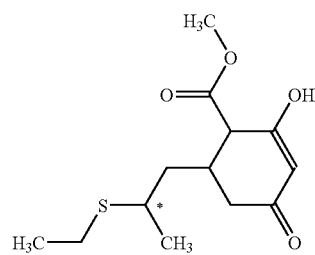
(VI)

f) Trione Synthesis

The formula VI intermediate is combined with propionic anhydride (ca. equal molar amounts), toluene and 4-(dimethylamino)pyridine (ca. 10 mole %), and stirred under heat. Reaction completion, yielding the adduct of formula VII, is verified by thin layer chromatography.

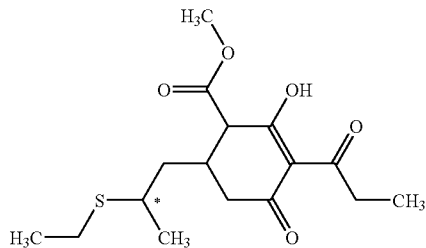
(VII)

The carbomethoxy group, as depicted in formula VII, is removed by cooling the adduct to ambient temperature, and then adding sodium hydroxide (25% solution; ca. 4 molar equivalents). The exotherm (ca. 10–20° C.) is permitted to proceed unchecked. The mixture is then stirred under heat. Thereafter, it is cooled to ambient temperature, separated and the organic layer is discarded. To the aqueous layer is added hexanes and then heat. Concentrated hydrochloric acid is added to reduce the mixture to an acidic pH and facilitate decarboxylation. This mixture is then stirred under heat to assure completion of decarboxylation. It is then cooled to ambient temperature, separated, and the aqueous layer is discarded. The organic layer is dried over sodium sulfate, filtered and stripped on a rotary evaporator to yield an amber oil, formula VIII.

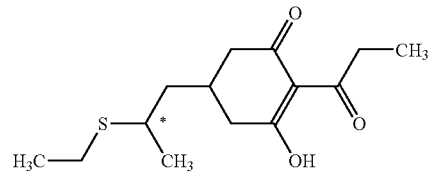
(VIII)

g) Clethodim Synthesis

The formula VIII trione intermediate and O-(3-Chloro-2-propenyl)hydroxylamine (CPHA) (ca. equal molar amounts) are reacted in a mixed hexanes-water system that has been adjusted to pH 5.5–6.0, with sodium hydroxide, and buffered by addition of acetic acid. The exotherm (ca. 5–10° C.) is permitted to proceed unchecked. The reaction mixture is then stirred overnight at ambient temperature. Reaction completion is verified by HPLC analysis. The aqueous layer is separated and discarded. To the organic layer is added water and then sodium hydroxide to pH 12–14. The organic layer is separated and discarded. To the aqueous layer is added hexanes and then concentrated hydrochloric acid to obtain an acidic pH. The aqueous layer is separated and discarded. The organic layer is washed with water and then dried over sodium sulfate and stripped to yield an amber oil.

Analysis of the resulting (−)-enantiomer includes verification of generic identity by NMR analysis and determination of chiral identity by specific rotation and separation under chiral HPLC conditions to determine enantiomeric excesses. Equal and opposite specific rotations $[\alpha]_D^{24} = 28°$ (C=ca. $6 \times 10^{-3}$ M in methanol) are determined on a polarimeter.

Production of Herbicidally-Effective Formulations Comprising (−) Clethodim Substantially Free of (+) Clethodim The preferred herbicidal composition is comprised of (−) clethodim substantially free of (+) clethodim, as defined above. The amount of (−) clethodim substantially free of (+) clethodim contained in herbicidal compositions of the present invention can be readily determined for particular crop plants and particular weed families by persons skilled in the art, depending on many factors, including the species of plant and its growth stage, row and plant spacing, environmental conditions, weather, etc. In general, however, it has been determined that suitable ranges of (−) clethodim substantially free of (+) clethodim in herbicidal compositions of the present invention are from about 0.010 to 0.25 pounds active ingredient per acre (lbai./A), preferably from about 0.022 to 0.12 lbai./A, more preferably from about 0.045 to 0.094 lbai./A, with more preferred ranges depending upon application, as discussed herein below.

While the herbicidal composition comprising a herbicidally-effective amount of (−) clethodim substantially free of (+) clethodim may be comprised solely of (−) clethodim, it is preferred that the formulation also includes one or more adjuvants. Useful adjuvants include, without limitation, crop oil concentrates, surfactants, fertilizers, emulsifiers, dispersing agents, foaming activators, foam suppressants, and correctives. Adjuvants generally facilitate the entry of (−) clethodim through plant cell walls. The usefulness of a particular adjuvant depends on, among other factors, the species of the plant being treated with the aforementioned formulation, the plant's growth stage and the related environmental conditions.

In a preferred embodiment, the one or more adjuvants in the herbicidal composition is a crop oil concentrate. Crop oil concentrates are generally comprised of from 65–96% by weight of a hydrocarbon oil or solvent with the balance being a surfactant. The hydrocarbons may be petroleum or vegetable based. Exemplary crop oil concentrates found to be useful in the formulations of this invention include Agridex (HELENA Chemical Co.). Preferably between about 0.05 and 5% v/v of a crop oil concentrate is included in the herbicidally-active formulation of the present invention. More preferably, the crop oil concentrate is 0.5 to 1.5% v/v, most preferably the crop oil concentrate is 1% v/v.

In a preferred embodiment, the herbicidally-effective composition is produced by mixing (−) clethodim substantially free of (+) clethodim into a spray mixture by adding, on a acre equivalent basis, half of the required water, the clethodim dose, and the adjuvant, and then bringing the mixture to 100% by adding the remaining amount of water.

Although one of ordinary skill in the art will understand that various volumes of the herbicidally-effective formulation may be prepared, depending on the size of the area to be treated, 20 gallons is a useful volume. As such, this embodiment of the herbicidally-effective composition can be produced by adding 10 gallons of water to a spray tank. Next, between about 0.010 to 0.25 pounds (−) clethodim substantially free of (+) clethodim, preferably between about 0.022 to 0.12 pounds, more preferably between about 0.045 to 0.094 pounds, are mixed into the tank. Then, between about 1 and 100 ounces of a crop oil concentrate, preferably between about 10 to 50 ounces, most preferably about 25 ounces, is mixed into the solution. Finally, water is added to bring the final volume to 20 gallons.

One of ordinary skill in the art will understand that (−) clethodim substantially free of (+) clethodim can be used as the only active ingredient in a herbicidal composition, or that it can be used in combination with one or more other active chemicals. As used in the present invention, the term "other active chemicals" refers to other chemicals that possess biological activity, such as plant disease control agents including insecticides, fungicides, bacteriocides, nematicides, and other herbicides.

In a preferred embodiment, the one or more other active chemicals in the herbicidally-effective composition is a secondary herbicide. Non-limiting examples of acceptable secondary herbicides include 2,4-DB, Assure®/Assure II, Basagran®, Classicg, Cobra®, Firstrate®, Fusilade®DX, Option®, Passport®, Pinnacleg, Pursuit®, Pursuit Plus®, Reliance™ STS®, Roundup Ultra®, Scepter®, Stellar®, and Synchrony™ STS®. A herbicidally-effective composition containing a secondary herbicide is produced by mixing the secondary herbicide into water, followed (−) clethodim substantially free of (+) clethodim, and a crop oil concentrate (if any). For a 15 gallon herbicidally-effective formulation, the mixture can be produced by mixing between about 0.005 and 10 pounds of the secondary herbicide active ingredient into 15 gallons of water, more preferably between about 0.5 and 5 pounds, most preferably about 1 pound. The remaining ingredients are then mixed into the formulation as directed above.

One of ordinary skill in the art will also understand that biologically inert carriers may be included in all embodiments of the herbicidal compositions of the present invention. Other active chemicals or inert ingredients may be used to provide a more satisfactory formulation, provided the chemicals or ingredients do not detract from the effect of the essential components of the invention.

Application of Herbicidally-Effective Formulations Comprising (−) Clethodim Substantially Free of (+) Clethodim One of ordinary skill in the art will understand that these methods described herein may be practiced by applying a formulation comprising (−) clethodim substantially free of (+) clethodim alone, although it is preferred that at least one adjuvant is present in the formulation. The methods may be practiced by applying a herbicidally-effective composition comprising (−) clethodim substantially free of (+) clethodim, one or more adjuvants, with or without other active chemicals, and with or without other inert ingredients. Furthermore, it will be understood that the (−) clethodim substantially free of (+) clethodim, one or more adjuvants, other active chemicals, and other inert ingredients may be applied concurrently or sequentially (in any desired sequence) so long as each component will perform as intended in accordance with the invention. If applied sequentially, the individual components may be applied over a short or long time frame.

The herbicidally-effective formulation may be applied to the surface of the plant in a single application until the leaves of the plant are partially wetted, fully wetted or until runoff. The formulation may be applied at any time of day or night with good resulting activity, but preferentially should not be applied within 30 minutes of a predicted rainfall. The application can be repeated as often as considered useful. In a preferred embodiment, the formulation is applied by spraying the formulation onto the plants. Non-limiting examples of means for spraying the formulation onto plants include a tractor boom sprayer, a hand held aerosol sprayer, air blast sprayer, and helicopter or fixed-wing aircraft boom sprayer. Preferably, the sprayer is calibrated to deliver the formulation at between about 1 and 100 gallons per acre, more preferably between about 3 and 40 gallons per acre, most preferably about 20 gallons per acre.

It will be apparent to one of ordinary skill in the art that the "herbicidally-effective amount" of (−) clethodim substantially free of (+) clethodim required to control plant growth will be largely variable, depending on many factors, including the species of plant and its growth stage, row and plant spacing, environmental conditions, weather, etc. In general however, it has been determined that a herbicidally-effective composition comprised of (−) clethodim substantially free of (+) clethodim, applied in amounts generally between about 0.01 and 0.25 pounds active ingredient per acre, adequately controls the growth of plants to which it is applied. More preferably, between about 0.022 and 0.12 pounds active ingredient per acre is used to control plant growth. Most preferably, about from 0.045 to 0.094 pounds active ingredient per acre is used to control plant growth.

In a preferred embodiment, the herbicidally-effective composition applied to plants is comprised of (−) clethodim substantially free of (+) clethodim and a crop oil concentrate. Preferably, the (−) clethodim substantially free of (+) clethodim of the composition is applied within the range discussed above. Preferably, the crop oil concentrate of the composition is applied at a rate of between about 1 and 100 fluid ounces per acre, more preferably between about 10 and 50 fluid ounces per acre, most preferably about 25 fluid ounces per acre.

Again, it is anticipated that within these general guidelines, one of ordinary skill in the art would be readily able to select an appropriate formulation and application volume per acre.

EXAMPLE 1

To a 3-L three-necked round-bottomed flask, equipped with a mechanic agitator, thermometer, dropping funnel, and cooling bath, were added 1500 g of 28% O-(3-chloro-2-propenyl)hydroxylamine hydrochloride aqueous solution containing 3% HCl, by weight. After the solution was cooled to 15° C., 50% sodium hydroxide, by weight, was gradually added under cooling and stirring to bring pH to about 0.1–3.5, maintaining reactor temperature below 40° C. To this mixture a total of 750 g of O-(3-chloro-2-propenyl)acetoxime was added. The mixture was vigorously agitated for 30 minutes and settled for 30 minutes.

After phase separation, the aqueous phase was transferred to a 2-L distillation unit equipped with a magnetic stirrer, thermometer, vacuum capability, and a 1 inch, 10-tray Oldershaw column. Vacuum was pulled to 60 torr before heating up. Reflux ratio was set to 3:1. The distillation was continued until there was no O-(3-chloro-2-propenyl)acetoxime coming into the distillate. After being cooled down to near ambient temperature, the solution in the still was transferred to a 2-L three-necked round-bottomed flask, equipped with a mechanic agitator, thermometer, dropping funnel, and cooling bath. After adding 100 g of DI water, 50% NaOH solution, by weight, was introduced gradually, maintaining reactor temperature below 40° C. The caustic addition and agitation were discontinued when the pH reached about 9.0. The mixture was settled for 30 minutes for complete phase separation. A total of 251 g of organic phase was obtained. Titration indicated 84% concentration of O-(3-chloro-2-propenyl)hydroxylamine (CPHA), by weight. Gas chromatographic (GC) analysis indicated above 99.9% purity, by GC area. In comparison with the original 1.42 mole % hydroxylamine, there was no hydroxylamine detected in the 84% organic phase by the method of ketone derivatization (oximation) and GC. No organic impurities were detected by GC.

The GC method set up for CPHA purity, impurity profile, and hydroxylamine content determination is described as follows.

Instrument: HP 6890 series GC system.
Column: HP-1 capillary column, 10 m×0.53 mm×2.651 m.
Detector: FID, 250° C.
Inlet: 200° C.
Oven Temperature program:
Initial temperature: 40° C.
Initial time: 2 minutes.
Ramps: 10° C./min, 65° C., 0 minutes
20° C./min, 250° C., 3 minutes.

The cyclohexanone derivatization method is described immediately below.

Weigh about 2.00 g of sample in a vial containing 2.20 g of cyclohexanone; Add 50% sodium hydroxide if necessary to bring pH to above 9. Stir the mixture in the capped vial at 50° C. for 2 hours. After cooling, add 8.0 g of dichloromethane and shake for one minute. Settle the mixture for 5 minutes. Take the organic phase for gas chromatographic (GC) analysis. CPHA purity and impurity profile are directly based on GC area. Hydroxylamine content is calculated based on the integration area of cyclohexanone oxime (cyclohexanoxime) peak and O-(chloro-2-propenyl)cyclohexanoxime peak.

The aqueous phase (1430 g) containing 6.7% of O-(3-chloro-2-propenyl)hydroxylamine (CPHA), by weight, is subject to distillation for recovery of CPHA.

EXAMPLE 2

To a 3-L three-necked round-bottomed flask, equipped with a mechanic agitator, thermometer, dropping funnel, and cooling bath, were added 1700 g of 38.6% O-(3-chloro-2-propenyl)hydroxylamine hydrochloride aqueous solution containing 4.6% HCl, by weight. To this solution a total of 1030 g of O-(3-chloro-2-propenyl)acetoxime was added. The mixture was vigorously agitated for 30 minutes and settled for 30 minutes.

After phase separation, the aqueous phase was transferred to a 2-L distillation unit equipped with a magnetic stirrer, thermometer, vacuum capability, and a 1 inch, 10-tray Oldershaw column. Vacuum was pulled to 77 torr before heating up. Reflux ratio was set to 3:1. The distillation was continued until there was no O-(3-chloro-2-propenyl)acetoxime coming into the distillate. After being cooled down to near ambient temperature, the solution in the still was transferred to a 3-L three-necked round-bottomed flask, equipped with a mechanic agitator, thermometer, dropping funnel, and cooling bath. After adding 400 g of DI water, 50% NaOH solution, by weight, was introduced gradually, maintaining reactor temperature below 40° C. The caustic addition and agitation were discontinued when the pH reached 9.0. The mixture was settled for 30 minutes for complete phase separation. A total of 403.2 g of organic phase was obtained. Titration indicated 84.5% concentration of O-(3-chloro-2-propenyl)hydroxylamine (CPHA), by weight. From the 2232 g of aqueous phase, containing 6.66% of O-(3-chloro-2-propenyl)hydroxylamine (CPHA), by weight, 892.8 g was sent to a 1-L distillation unit. After the overhead splitter was set in total take-off mode, the still was heated to boiling. The distillation was continued until there was not noticeable CPHA coming into the distillate. A total of 288.9 g of distillate was collected with a concentration of 19.4%, by weight, and a yield of 94.2%, by weight. GC analysis indicated above 99.9% purity, by gas chromatographic area. No hydroxylamine and organic impurities were detected in the distillate.

EXAMPLE 3

To a 1-L three-necked round-bottomed flask, equipped with a mechanic agitator, thermometer, dropping funnel, and cooling bath, were added 400 g of 40.5% O-(3-chloro-2-propenyl)hydroxylamine hydrochloride aqueous solution containing 4.7% HCl, by weight. To this solution a total of 250 g of O-(3-chloro-2-propenyl)acetoxime was added. The mixture was vigorously agitated for 30 minutes and settled for 30 minutes.

After phase separation, the aqueous phase was transferred to a 500 mL distillation unit equipped with a magnetic stirrer, thermometer, vacuum capability, and a 1 inch, 10-tray Oldershaw column. Vacuum was pulled to 60 torr before heating up. Reflux ratio was set to 3:1. The distillation was continued until there was no O-(3-chloro-2-propenyl)acetoxime coming into the distillate. After being cooled down to near ambient temperature, the solution in the still was transferred to a 1-L three-necked round-bottomed flask, equipped with a mechanic agitator, thermometer, dropping funnel, and cooling bath. After adding 107 g of DI water, 50% NaOH solution, by weight, was introduced gradually, maintaining reactor temperature below 40° C. The caustic addition and agitation were discontinued when the pH reached 9.0. The two-phase mixture was sent to a 1-L distillation unit. After the overhead splitter was set in total take-off mode and 200 g of water was added, the still was heated to boiling. The distillation was continued until there was not noticeable CPHA coming into the distillate. A total of 492.5 g of distillate was collected with a concentration of 23.3%, by weight, and a yield of 94.7%, by weight. GC analysis indicated above 99.9% purity, by gas chromatographic area. No organic impurities and hydroxylamine were detected in the distillate.

EXAMPLE 4

Charge a 1-L simple distillation unit with 690 g of 84.2% O-(3-chloro-2-propenyl)hydroxylamine (CPHA) aqueous solution obtained from a run described in Example 2. After the system was vacuumed to 70 torr and condenser coolant applied, the still was heated to boiling. Distillate was taken in cuts over time and vacuum was adjusted to maintain still temperature below 65° C. When the overhead temperature reached 42° C./1 torr, the main cut was started. A total of 475.7 g of anhydrous main cut was collected with a concentration of 97%, d 1.18.

This compound is soluble in many organic solvents, such as ethers, alcohol, toluene, and chlorinated alkanes. For example, to make a O-(3-chloro-2-propenyl)hydroxylamine solution in dichloromethane, CPHA is simply mixed with dichloromethane. No exotherm was observed.

What is claimed is:

1. An O-substituted hydroxylamine free base composition having the following general formula:

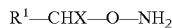

$R^1$—CHX—O—NH$_2$ wherein X is hydrogen or an alkyl; and $R^1$ is an unsubstituted or substituted phenyl, thienyl, furanyl, pyrrolyl or —$CR^2$=$CR^3R^4$; wherein $R^2$, $R^3$ and $R^4$ are hydrogen, halogen or alkyl; and wherein said O-substituted hydroxylamine exhibits at least one property selected from the group consisting of:

essentially free of hydroxylamine;

essentially free of any solvent;

a water content of between about 0% to 90% by weight; and a high strength (as measured by mole of said O-substituted hydroxylamine per gram of sample) of between about 0.5 to 3.3-fold as much as a 40% O-substituted hydroxylamine salt solution, by weight.

2. The composition according to claim 1, wherein said O-substituted hydroxylamine is at least one isomer selected from the group consisting of cis, trans and a mixture thereof.

3. The composition according to claim 1, wherein said O-substituted hydroxylamine has at least one additional property selected from the group consisting of:

a purity of between about 98% to 100%, based on gas chromatographic area; and a purity drop of less than about 1.2% after 78 days at 40° C. when said O-substituted hydroxylamine has a concentration of about 85% in water, based on gas chromatographic area.

4. The composition according to claim 1, wherein said O-substituted hydroxylamine is O-(3-chloro-2-propenyl)hydroxylamine.

5. The composition according to claim 1, wherein said O-substituted hydroxylamine is formed by the following steps comprising:

a. optionally admixing an organic solvent with a solution of O-substituted hydroxylamine salt to form at least an aqueous phase and extracting impurities from said aqueous phase;

b. optionally stripping residual organic solvents from said aqueous phase to form an aqueous-enriched phase;

c. adjusting the pH of said aqueous-enriched phase to a pH of at least about 3.5, thereby forming an organic-enriched stream and an aqueous phase stream; and d. separating said O-substituted hydroxylamine from said organic-enriched stream and/or said aqueous phase stream.

6. The composition according to claim 5, wherein said organic solvent used in extraction step (a) is selected from the group consisting of: aliphatic compounds, aromatic compounds, and alicyclic compounds.

7. The composition according to claim 5, wherein the extraction step (a) is conducted at a pH of about 7 or less.

8. The composition according to claim 7, wherein said pH is less than about 4.

9. The composition according to claim 5, wherein the extracting step (a) is conducted at a temperature between about −10 to 97° C.

10. The composition according to claim 5, wherein said O-substituted hydroxylamine salt is O-substituted hydroxylamine hydrochloride.

11. The composition according to claim 10, wherein said O-substituted hydroxylamine hydrochloride is O-(3-chloro-2-propenyl)hydroxylamine hydrochloride.

12. The composition according to claim 5, wherein the extracting step (a) is conducted at a pressure between about 0 to 15 atmospheric pressure (atm).

13. The composition according to claim 5, wherein said separating step (d) comprises at least one step selected from the group consisting of:

(i) separating said organic-enriched stream from said aqueous phase stream, wherein said organic-enriched stream comprises said O-substituted hydroxylamine;

(ii) distilling said aqueous stream, wherein said O-substituted hydroxylamine is taken overhead;

(iii) optionally, distilling said organic-enriched stream and said aqueous phase stream from the pH adjustment step (c), wherein said O-substituted hydroxylamine is taken overhead; and (iv) optionally, fractionally distilling said organic-enriched stream, wherein a substantially solvent-free O-substituted hydroxylamine is taken overhead.

14. The composition according to claim 13, wherein said phase separation step (i) is conducted at a pH of between about 3.5 to 14.

15. The composition according to claim 14, wherein the pH during said phase separation step (i) is between about 4.5 to 13.

16. The composition according to claim 13, wherein the phase separation step (i) is conducted at a temperature of between about −10° C. to 97° C.

17. The composition according to claim 13, wherein the phase separation step (i) is conducted at a pressure between about 0 to 15 atm.

18. The composition according to claim 13, wherein said distilling step (ii) is conducted via distillation.

19. The composition according to claim 18, wherein said distillation comprises at least a column, a condenser, a reflux ratio controller, and a receiver.

20. The composition according to claim 19, wherein said column comprises about 0 to 35 theoretical plates.

21. The composition according to claim 20, wherein column comprises about 5 to 15 theoretical plates.

22. The composition according to claim 13, wherein said distilling step (ii) is conducted at a pressure between about 5 to 800 torr.

23. The composition according to claim 13, further comprising the addition of water during said distilling step (ii).

24. The composition according to claim 13, wherein said distilling step (iii) is conducted at a pressure between about 5 to 800 torr.

25. The composition according to claim 13, wherein said distilling step (iv) is conducted at a pressure between about 0 to 100 torr.

26. The composition according to claim 5, wherein said aqueous-enriched phase is adjusted to a pH between about 3.5 to 14.

27. The composition according to claim 26, wherein said pH of said aqueous-enriched phase is adjusted to between about 4.5 to 13.

28. The composition according to claim 27, wherein said pH of said aqueous-enriched phase is adjusted to between about 6.5 to 13.

29. The composition according to claim 5, wherein said pH adjusting step (c) is conducted at a temperature between about −10° C. to 97° C.

30. An O-substituted hydroxylamine free base composition having the following general formula:

$R^1$—CHX—O—$NH_2$ wherein X is hydrogen or an alkyl; and $R^1$ is an unsubstituted or substituted phenyl, thienyl, furanyl, pyrrolyl or —$CR^2$=$CR^3R^4$; wherein $R^2$, $R^3$ and $R^4$ are hydrogen, halogen or alkyl; and wherein said O-substituted hydroxylamine is essentially free of hydroxylamine.

31. An O-substituted hydroxylamine free base composition having the following general formula:

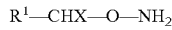
$R^1$—CHX—O—$NH_2$ wherein X is hydrogen or an alkyl; and $R^1$ is an unsubstituted or substituted phenyl, thienyl, furanyl, pyrrolyl or —$CR^2$=$CR^3R^4$; wherein $R^2$, $R^3$ and $R^4$ are hydrogen, halogen or alkyl; and wherein said O-substituted hydroxylamine is essentially free of any solvent.

32. An O-substituted hydroxylamine free base composition having the following general formula:

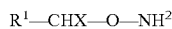
$R^1$—CHX—O—$NH^2$ wherein X is hydrogen or an alkyl; and $R^1$ is an unsubstituted or substituted phenyl, thienyl, furanyl, pyrrolyl or —$CR^2$=$CR^3R^4$; wherein $R^2$, $R^3$ and $R^4$ are hydrogen, halogen or alkyl; and wherein said O-substituted hydroxylamine has a water content of between about 0% to 90% by weight.

33. An O-substituted hydroxylamine free base composition having the following general formula:

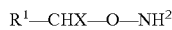
$R^1$—CHX—O—$NH^2$ wherein X is hydrogen or an alkyl; and $R^1$ is an unsubstituted or substituted phenyl, thienyl, furanyl, pyrrolyl or —$CR^2$=$CR^3R^4$; wherein $R^2$, $R^3$ and $R^4$ are hydrogen, halogen or alkyl; and wherein said O-substituted hydroxylamine has a high strength (as measured by mole of said O-substituted hydroxylamine per gram of sample) of between about 0.5 to 3.3-fold as much as a 40% O-substituted hydroxylamine salt solution, by weight.

34. The composition according to claim 3, wherein said O-substituted hydroxylamine is O-(3-chloro-2-propenyl)hydroxylamine.

35. The composition according to claim 5, wherein said aqueous-enriched phase in step (c) is an O-substituted hydroxylamine salt.

36. The composition according to claim 35, wherein said O-substituted hydroxylamine salt is O-substituted hydroxylamine hydrochloride.

37. The composition according to claim 36, wherein said O-substituted hydroxylamine hydrochloride is O-(3-chloro-2-propenyl)hydroxylamine hydrochloride.

38. An O-substituted hydroxylamine salt composition having the following general formula:

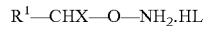
$R^1$—CHX—O—$NH_2$.HL wherein L is a halogen or hydrogensulfate; X is hydrogen or alkyl; $R^1$ is unsubstituted or substituted phenyl, thienyl, furanyl, pyrrolyl or —$CR^2$=$CR^3R^4$; wherein $R^2$, $R^3$, and $R^4$ are each hydrogen, halogen or alkyl; and wherein said O-substituted hydroxylamine salt is essentially free of hydroxylamine.

39. The O-substituted hydroxylamine salt composition according to claim 38, wherein said O-substituted hydroxylamine salt is at least one isomer selected from the group consisting of cis, trans and a mixture thereof.

40. The O-substituted hydroxylamine salt composition according to claim 38, wherein said O-substituted hydroxylamine salt is O-(3-chloro-2-propenyl)hydroxylamine hydrochloride.

41. The O-substituted hydroxylamine salt composition according to claim 38, wherein said O-substituted hydroxylamine salt is formed by the following steps comprising:
a. optionally admixing an organic solvent with an hydroxylamine-containing O-substituted hydroxylamine salt to form at least an aqueous phase and extracting impurities from said aqueous phase;
b. optionally stripping residual organic solvents from said aqueous phase to form an aqueous-enriched phase;
c. adjusting the pH of said aqueous-enriched phase to a pH of at least about 3.5, thereby forming an organic-enriched stream and an aqueous phase stream;
d. separating said O-substituted hydroxylamine from said organic-enriched stream and/or said aqueous phase stream; and
e. reacidifying said O-substituted hydroxylamine, thereby forming said O-substituted hydroxylamine salt which is essentially free of hydroxylamine.

42. The O-substituted hydroxylamine salt composition according to claim 41, wherein step (e) is conducted at a temperature of about 75° C. or less.

43. The O-substituted hydroxylamine salt composition according to claim 42, wherein step (e) is conducted at a temperature of about 65° C. or less.

* * * * *